United States Patent [19]

Orsolini et al.

[11] Patent Number: 5,776,885
[45] Date of Patent: Jul. 7, 1998

[54] SUSTAINED AND CONTROLLED RELEASE OF WATER INSOLUBLE POLYPEPTIDES

[75] Inventors: Piero Orsolini, Martigny; Rolland-Yves Mauvernay; Romano Deghenghi, both of Lausanne, all of Switzerland

[73] Assignee: Debio Recherche Pharmaceutique SA, Martigny, Switzerland

[21] Appl. No.: 196,872

[22] Filed: Feb. 10, 1994

Related U.S. Application Data

[60] Continuation of Ser. No. 915,491, Jul. 16, 1992, abandoned, which is a division of Ser. No. 247,060, Sep. 20, 1988, Pat. No. 5,192,741.

[30] Foreign Application Priority Data

Sep. 21, 1988 [GB] United Kingdom ............... 8722134

[51] Int. Cl.$^6$ .......................... A61K 38/04; A61K 9/52
[52] U.S. Cl. .......................... 514/2; 514/15; 514/16; 514/17; 514/18; 424/409; 424/417; 424/490; 424/491
[58] Field of Search .......................... 514/2, 15–19; 424/490, 417, 409, 491

[56] References Cited

U.S. PATENT DOCUMENTS

| | | | |
|---|---|---|---|
| 4,010,125 | 3/1977 | Schally et al. | 260/8 |
| 4,341,767 | 7/1982 | Nestor | 424/177 |
| 4,526,938 | 7/1985 | Churchill | 525/415 |
| 4,622,244 | 11/1986 | Lapka et al. | 427/213.32 |
| 4,673,595 | 6/1987 | Orsolini | 427/213.32 |
| 4,675,189 | 6/1987 | Kent et al. | 424/490 |
| 4,677,193 | 6/1987 | Rivier | 530/313 |
| 4,708,861 | 11/1987 | Popescu | 424/1.1 |
| 4,745,160 | 5/1988 | Churchill | 525/415 |
| 4,767,628 | 8/1988 | Hutchison | 424/426 |
| 4,835,139 | 5/1989 | Tite | 514/15 |
| 4,954,298 | 9/1990 | Yamamoto | 264/4.6 |
| 5,089,471 | 2/1992 | Hanson | 514/11 |
| 5,140,011 | 8/1992 | Branca | 514/18 |

FOREIGN PATENT DOCUMENTS

| | | | |
|---|---|---|---|
| 52510 | 6/1982 | European Pat. Off. | A61K 9/50 |
| 58481 | 8/1982 | European Pat. Off. | A61K 37/02 |
| 204476 | 12/1986 | European Pat. Off. | A61K 9/00 |
| 0 211 267 | 2/1987 | European Pat. Off. | A61K 37/02 |
| 251176 | 1/1988 | European Pat. Off. | A61K 9/22 |
| 302582 | 2/1989 | European Pat. Off. | A61K 9/54 |
| 1325209 | 8/1973 | United Kingdom . | |

OTHER PUBLICATIONS

Chang, "Biodegradable Semipermeable Microcapsules Containing Enzymes, Hormones, Vaccines and Other Biologicals", J. Bioeng. 1 (1976) p. 25.

Langer, "Controlled Release of Macromolecules", Chemtech Feb. 1982 pp. 98–105.

Hutchison et al., "Biodegradable Carriers for the Sustained Release of Polypeptides", TIBTECH Apr. 1987 (vol. 5) pp. 102–106.

Chemical Abstracts, vol. 107, No. 13, Abstract 109765g (1987).

*Primary Examiner*—David Lukton
*Attorney, Agent, or Firm*—Pennie & Edmonds LLP

[57] ABSTRACT

A pharmaceutical composition for the sustained release of a peptide wherein the composition includes a polylactide polymer, a polymer of lactic acid and glycolic acid, or a mixture of such polymers and a therapeutically active peptide in the form of its pamoate, tannate or stearate salt. The composition when placed in an aqueous physiological environment releases the peptide in a continuous manner for a period of at least about one week.

12 Claims, No Drawings

SUSTAINED AND CONTROLLED RELEASE OF WATER INSOLUBLE POLYPEPTIDES

This is a continuation of application Ser. No. 07/975,497 filed Jul. 16, 1992, now abandoned, which in turn is a divisional of application Ser. No. 07/247,060, filed Sep. 20, 1998, now U.S. Pat. No. 5,192,741.

FIELD OF THE INVENTION

This invention relates to pharmaceutical compositions of therapeutically active but water-insoluble polypeptides, which provide a continuous, controlled and sustained release of such peptides when placed in a physiological-type environment by means of implant or injections under the skin or into the muscle of animals and humans.

This invention is further characterized by the use of bio-degradable and bio-compatible polymers and copolymers as matrix in which the water-insoluble polypeptides are dispersed or encapsulated.

BACKGROUND OF THE INVENTION

The need of producing sustained release of peptides for parenteral administration has been recognized for a long time (cf. T. M. S. Chang "Biodegradable Semipermeable Microcapsules containing enzymes, hormones, vaccines and other biologicals" in J. Bioengineering 1, 25 (1976); R. Langer "Controlled Release of Macromolecules" in Chemtech, February 1982, pp 98–105; F.G. Hutchinson and B.J. A. Furr "Biodegradable carriers for the sustained release of polypeptides" in TIBTECH, April 1987 (vol.5) pp 102–106.

A number of such formulations, but applied to water soluble polypeptides, have been described in EPS 0052510 "Microencapsulation of water soluble polypeptides", published Aug. 27, 1986 and in EPS 0058481 "Continuous release pharmaceutical compositions", published Oct. 1, 1986.

SUMMARY OF THE INVENTION

The novel, surprising and totally unexpected feature of the present invention resides in the fact that therapeutically useful sustained and controlled release compositions can advantageously be obtained by using essentially water-insoluble peptides, possessing immeasurably low solubility in aqueous solution at room or body temperature and yet providing an effective and controlled release of such peptides when their compositions are administered parenterally in a physiologic, essentially aqueous environment.

DETAILED DESCRIPTION OF THE PREFERRED EMBODIMENTS

It is a novel and surprising consequence of the present invention that polypeptides which are normally water soluble in nature or when prepared by synthesis, can be advantageously rendered water insoluble by forming insoluble addition salts, such as with pamoic acid, tannic acid, stearic acid and other non-toxic water-insoluble acids, prior to their microencapsulation or dispersion in a biodegradable polymeric matrix.

The use of sparingly soluble or water insoluble derivatives is of course well known, even in the peptide field (cf Schally et al. U.S. Pat. No. 4,010,125 Mar. 1, 1977, column 7, line 25), when slow-release depot dosage forms are needed.

However, when biodegradable polymers such as polylactic acid, polyglycolic acid, polyhydroxybutyric acid, polyortho-esters, polyacetals and the like are used as drug delivery systems, the release of the peptides in a continuous manner has consistently required an appreciable water solubility. Reported experiments have shown that the biodegradation of polymers (such as polylactide and polylactide-coglycolide for example) leads to water-uptake and generation of aqueous channels or pores from which peptides leak out because they are water soluble.

Our discovery that peptides can be released from matrixes and microcapsules with a highly desirable release pattern when their water solubility is diminished down to practically zero levels is totally surprising and contradicts the teachings of the prior art. In particular we found that the release of certain peptides, such as D-Trp$^6$-LHRH, from polymeric matrixes, is better in terms of uniformity and duration, the more water-insoluble the addition salt of the peptide is.

"Water-insolubility" is hereby defined as the amount of peptide which can be measured in solution when the salt is dispersed or stirred for 4 hours in distilled water at temperatures of 40° C. or below, such amount being 25 mg/l or less (0 to 25 ppm).

It is highly desirable to administer biologically active polypeptides continuously and for a sustained period of time, from one week to several months. It is also highly desirable that the pattern of release be controlled, so as to avoid uneven releases of the peptide at the beginning, in the middle or at the end of the therapeutic cycle. It has been often found that peptides are released from biodegradable matrixes in bursts (also called burst effects), either at the beginning of the cycle or at the end, when the polymeric matrix is eroded through hydrolysis.

An important feature of the present invention is a control of the release pattern, and in general a decrease of the initial burst effect. The water insoluble peptide is released to a lesser extent that its water soluble derivatives, thus affording a more prolonged release time and the avoidance of overdosing the patient. By transforming a normally water soluble peptide into an insoluble one, we are able to limit the initial burst effect (i.e. the amount of peptide released in the first 24 hours) to less than 30% of the total dose.

EXAMPLE I

Fifty grams of a copolymer of D,L-lactide and glycolide with a 50/50 molar ratio of D,L-lactide to glycolide and an average molecular weight of 50,000 is dissolved in 950 grams of methylene chloride.

The solution is passed through a millipore filter to remove any particulate matter and pyrogens. To this solution, one gram of D-Trp$^6$ LHRH pamoate is added and dispersed with a high shear mixer.

The resulting mixture is placed in a rotating evaporator and the majority of the methylene chloride is removed under vacuum. The resulting thick dispersion is poured onto a glass plate and spread with an adjustable blade set at 0.7 mm.

After air drying the resulting film is vacuum desiccated for 48 hours and then extruded through a 0.8 mm orifice at 70° C. under pressure. The resulting rods are ground cryogenically at −40°C.

The resulting granular material is sieved through a 180 micrometer screen and the undersize fraction is collected and sterilized by exposure to gamma radiation between 2.5 and 2.8 Mrad.

EXAMPLE II

The same procedure as in example I is followed by substituting D-Trp$^6$-LHRH pamoate with D-Trp$^6$-LHRH stearate salt.

EXAMPLE III

The same procedure as in example I is followed with the pamoate salt of

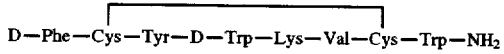
D—Phe—Cys—Tyr—D—Trp—Lys—Val—Cys—Trp—NH$_2$ as the water insoluble peptide.

EXAMPLE IV

The procedure of example I is applied to one of following water-insoluble pamoate salts:

D-Nal (2)$^6$ LHRH pamoate

D-Ser(0-tBu)$^6$-des Gly$^{10}$-Azgly$^{10}$-LHRH pamoate

D-Ser(Bu$^t$)$^6$ LHRH(1-9) ethylamide pamoate

D-Leu$^6$-des Gly$^{10}$-LHRH ethylamide pamoate

EXAMPLE V

The procedure of examples I to IV is followed with D.L lactide-co-glycolide polymers in which the molar ratio was 67% D.L lactide 33% glycolide, 75% D.L lactide 25% glycolide or 100% D.L lactide.

EXAMPLE VI

The procedure of examples I to V is followed with the waterinsoluble pamoate, tannate or stearate salts of one of the following peptides: oxytocin, vasopressin, ACTH, calcitonin, epidermal growth factor, prolactin, inhibin, interferon, LHRH, somatostatin, insulin, glucagon, atrial natriuretic factor, endorphin, a renin inhibitor, GHRH, peptide-T, or synthetic analogues and modifications thereof.

RELEASE PATTERN IN ANIMALS (RATS)

A typical release pattern of an implanted formulation of D-Trp$^6$-LHRH pamoate in rats is the following: ng/ml of radio-assayed D-Trp$^6$-LHRH in plasma (mean of six rats): (t$_0$) 0.04, (1 hr) 7.74, (6 hrs) 0.80, (day 2) 0.85, (day 4) 0.77, (day 7) 0.25, (day 11) 0.12; (day 14) 0.11, (day 18) 0.11, (day 21) 0.14, (day 25) 0.18.

The preceding examples are not limitative to the described water-insoluble peptides or to the biodegradable polymers used, as it is apparent to a person skilled-in-the-art.

In an alternate embodiment of the invention, the composition is prepared by dispersing a water-insoluble peptide salt into a solution of a polyactide polymer, a polyglycolide polymer, a copolymer of lactic and glycolic acids or a mixture of such polymers and adding a coacervation agent to form a plurality of microcapsules. The resulting microcapsules, which may range in size from 1 to 500 μm, are poured into a pharmaceutically acceptable hardening liquid and then collected for use as the pharmaceutical composition.

We claim:

1. A dry pharmaceutical composition designed for sustained release of a water-insoluble peptide salt comprising a polylactide polymer, a polymer of lactic and glycolic acid, or a mixture of said polymers and a therapeutically active peptide in the form of its pamoate salt, which composition, when placed in an aqueous physiological environment, releases the peptide in a continuous manner for a period of at least one week followed by maintenance of activity of the peptide for at least one month.

2. A pharmaceutical composition as claimed in claim 1 in which the peptide salt is the pamoate salt of LHRH or a synthetically prepared analogue thereof.

3. A pharmaceutical composition as claimed in claim 1 in which the peptide is a pharmaceutically acceptable salt of oxytocin, vasopressin, ACTH, calcitonin, epidermal growth factor, prolactin, inhibin, interferon, somatostatin, insulin, glucagon, atrial natriuretic factor, endorphin, a renin inhibitor, growth hormone releasing hormone, peptide T or a synthetic analogue thereof.

4. A pharmaceutical composition as claimed in claim 1 in which the peptide salt is the pamoate salt of D-Trp$^6$-LHRH.

5. A pharmaceutical composition as claimed in claim 1 in which the peptide salt is the pamoate salt of D-Phe-Cys-Tyr-D-Trp-Lys-Val-Cys-Trp-NH$_2$.

6. A pharmaceutical composition as claimed in claim 1 wherein the composition is in the form of particles ranging in size from 1 to 500 μm.

7. A pharmaceutical composition as claimed in claim 1 in the form of a solid rod which is sterilized by gamma radiation.

8. A pharmaceutical composition as claimed in claim 1 wherein not more than 30% of the total amount of peptide is initially released during the first twenty-four hours.

9. A pharmaceutical composition as claimed in claim 1 in the form of a rod for use as a parenteral implant.

10. A pharmaceutical composition designed for sustained release of a peptide comprising a polylactide polymer, a polymer of a lactic and glycolic acid, or a mixture of said polymers and a therapeutically active peptide in the form of a water-insoluble pamoate salt, which composition, when placed in an aqueous physiological environment, releases the peptide in a continuous manner for a period of at least one week followed by maintenance of activity of the peptide for at least one month, wherein said pharmaceutical composition has been sterilized with gamma radiation and suspended in a pharmaceutically acceptable carrier.

11. A pharmaceutical composition as claimed in claim 10, wherein the peptide salt is dispersed within solid particles of the polymer.

12. A pharmaceutical composition as claimed in claim 11 wherein the peptide salt is the pamoate salt of D-Trp$^6$-LHRH, and the polymer is a D.L-lactide and glycolide polymer.

* * * * *